United States Patent [19]

Bar-Or

[11] Patent Number: 5,470,750

[45] Date of Patent: Nov. 28, 1995

[54] DETECTION OF APPENDICITIS BY MEASUREMENT OF ORTHOHYDROXYHIPPURIC ACID

[75] Inventor: David Bar-Or, Englewood, Colo.

[73] Assignee: Appenditech, Inc., Englewood, Colo.

[21] Appl. No.: 911,159

[22] Filed: Jul. 9, 1992

Related U.S. Application Data

[63] Continuation-in-part of Ser. No. 436,823, Nov. 15, 1989, abandoned.

[51] Int. Cl.$^6$ .......................... G01N 33/52; G01N 30/02; G01N 30/90; G01N 30/96

[52] U.S. Cl. .......................... 436/63; 435/10; 435/810; 436/8; 436/15; 436/86; 436/106; 436/173; 436/175; 436/178

[58] Field of Search .................. 435/4, 5, 6, 810, 435/10; 514/44, 1, 42; 436/501, 173, 8, 15, 63, 86, 106, 175, 178

[56] References Cited

U.S. PATENT DOCUMENTS 3,915,647 10/1975 Wright ........................... 23/253

FOREIGN PATENT DOCUMENTS 8901471 2/1989 WIPO.

OTHER PUBLICATIONS

Kaplan et al. (1989) Clin Chem Acta, vol. 185, pp. 119–130.
Kapp, E. M. & Coburn, A. F., Urinary Metabolism of Sodium Salicylate-J. Biol. Chem 124: 549–565, 1942.
Altschule, M. D. & Hegedus, Z. L., Ortho–hydroxyhippuric (salicyluric) acid and Itsphysiological and Clinical Significance; Clin. Pharm. and Therapeutics, 15: (2) 111–117 1974.

*Primary Examiner*—Margaret Parr
*Assistant Examiner*—Ardin H. Marschel

[57] ABSTRACT

Appendicitis can be detected in human beings suspected of having appendicitis by determining a threshold level of 10 mg/liter of σ-hydroxyhippuric acid in the urine of such humans. This threshold level can be determined by qualitative, semiquantitative, or quantitative methods including HPLC (high pressure liquid chromatography), TLC (thin layer chromatography), radioimmunoassay, colorimetric tests, NMR (nuclear magnetic resonance), mass spectrometry, electrophoresis, monoclonal antibody tests, and enzymatic tests. The absence of appendicitis can be established by the presence of σ-hydroxyhippuric acid in concentrations less than about 10 mg/liter in a urine sample.

18 Claims, 2 Drawing Sheets

---

Procedure A (PART A)

Step 1
Using a bulb dispenser add 10 to 15 drops of urine to the vial containing the yellow reagent.

Step 2
Mix gently and leave for 20-30 seconds.

Compare to the color chart below. A pink to brown or purple color indicates a positive test. For confirmation test part B should be used.

color comparison chart

COLOR COMPARISON CHART

←———— POSITIVE RANGE ————►◄———— NEGATIVE RANGE ————→

If in doubt use procedure B

Fig. 1

Procedure A (PART A)

Step 1
Using a bulb dispenser add 10 to 15 drops of urine to the vial containing the yellow reagent.

Step 2
Mix gently and leave for 20-30 seconds.

Compare to the color chart below. A pink to brown or purple color indicates a positive test. For confirmation test part B should be used.

color comparison chart

COLOR COMPARISON CHART

POSITIVE RANGE ← → NEGATIVE RANGE

If in doubt use procedure B

Fig. 2

Procedure B (PART B)

Stage 1
Step 1
Fill the buffered syringe with 1 ml of urine and mix until dissolved.

Step 2
Pass the sample through the extraction cartridge.

Step 3
Remove the plunger, add 1 ml of water. Replace plunger and disgard the waste.

Step 4
Remove the plunger and add 1 ml of the extraction solvent. Replace the plunger and collect the solvent in the empty vial for use later.

Stage 2
Step 1
Place the developing solvent in the glass tank and replace lid.

Step 2
Use the applicator to spot the sample in the area provided.

Step 3
Remove the plate from the holder and place in the tank. Allow the solvent to raise to the line, remove, then dry.

Stage 3
Step 1
Place 4-5 drops of the developer onto the swab provided.

Step 2
Wipe over the window area in one smooth movement.

Step 3
Colored spots will appear within a few seconds and can be compared to the illustrations in the instructions.

DETECTION OF APPENDICITIS BY MEASUREMENT OF ORTHOHYDROXYHIPPURIC ACID

This patent application is a continuation-in-part patent application of U.S. patent application 436,823 filed Nov. 15, 1989, now abandoned, and also entitled "Detection Of Appendicitis By Measurement of Orthohydroxyhippuric Acid."

BACKGROUND OF THE INVENTION

1. Technical Field

This invention generally relates to methods for determining the presence of appendicitis in human beings. More specifically, it is concerned with methods for determining the presence of appendicitis based upon chemical analysis of the urine of human beings suspected of having appendicitis. The significance of this invention follows from the fact that the diagnosis of appendicitis very often challenges a physician's ability to differentiate this disease from other abdominal or pelvic disorders such as abdominal aortic aneurysm, pelvic inflammatory disease, ectopic pregnancy, ruptured or perforated viscus, gastro-intestinal bleeding, hemorrhagic pancreatitis, perforated diverticulum, ovarian abscess, Crohn's disease, mesenteric adenitis intestinal obstruction, gastroenteritis, diverticulitis, ovarian cyst and tubo-ovarian pathology.

That is to say that were it not for the fact that such diseases often simulate appendicitis, and the fact that a fully developed picture is seldom available to the physician, a diagnosis of appendicitis would be relatively straightforward: confirmation of periumbilical pain of less than 72 hours duration, migration of such pain to the right lower quadrant in a patient with a temperature of 99.5° to 101.3° F., evidence of abdominal tenderness, abdominal rigidity, a right-lower-quadrant abdominal mass and the presence of a mass on rectal examination. The diagnostic indicators described above, when found, are representative for patients later described in this patent disclosure as "suspected of having appendicitis". In many respects, negative predictors of appendicitis are often more helpful in excluding appendicitis from a diagnosis. The most commonly employed negative predictors include: symptoms lasting more than 72 hours, pain at locations other then those noted above, temperature below 99.5° or above 101.3° F. and the absence of anorexia.

Unfortunately, neither leukocyte counts nor roentgenograms are sensitive or specific to appendicitis. Moreover, no reliable chemical tests for the detection of appendicitis have been heretofore developed. Hence, diagnosis of appendicitis is made almost solely on those clinical grounds noted above. Consequently, a large number of patients are taken to the operating room for explorative operations, with an average false positive experience of about 20%. This rather high false positive experience is tolerated because prompt action is needed to prevent this acute disease, curable by appendectomy, from advancing to one complicated by perforation, peritonitis, long-term sequelae, and even death.

In its most fundamental aspect, the practice of this invention enables the physician to correlate the presence of certain threshold concentration levels of σ-hydroxyhippuric acid with the presence of a particular disease state, namely, appendicitis. Applicant's findings are important because σ-hydroxyhippuric acid is normally formed in lesser concentrations by the body. Such formation is believed to occur chiefly through conjugation of orthohydroxybenzoic acid (salicylic acid) and glycine. The enzyme that catalyzes the reaction has been named glycine N-acylase and, as its name implies, its action leads to the formation of a number of different glycine conjugates. Hence, σ-hydroxyhippuric acid is a normal constituent of the urine in man, as well as in the urine of other animals such as the horse, and the dog. It is also found in cow's milk. However, those skilled in this art will appreciate that these observations, in and of themselves, permit no conclusions regarding the source of the compound in the urine, i.e., whether it was of dietary origin completely, or whether the σ-hydroxyhippuric acid was partly or entirely endogenous in origin. For example, some basic biochemical studies have shown that orthohydroxybenzoic acid may be formed via the acetate-malonate pathway as well as by the shikimic acid pathway. It has also been suggested that the compound may also be derived from tryptophan.

To a large extent, the urinary excretion of σ-hydroxyhippuric acid has been studied through the administration of salicylate and/or through the administration of σ-hydroxyhippuric acid itself. However, there is a much more limited body of knowledge regarding the physiologic and pathologic implications of excessive formation of σ-hydroxyhippuric acid as a manifestation of disease and distorted metabolic processes. For example it is known that σ-hydroxy-hippuric acid is both filtered 10 and secreted by the kidneys, secretion occurring, at least in the dog, when high blood levels occur. It also appears to accumulate in the cortex of rabbit kidney slices. Hypoxia seems to diminish this accumulation. When taken by mouth by human beings, σ-hydroxyhippuric acid is known to change, at least in part, back to salicylate. In the dog it depresses the excretion of para-amino-hippurate.

The presence or absence of σ-hydroxyhippuric acid in the urine of humans has been associated with certain specific disease states. These associations are well summarized in the literature, (see, generally, Clinical Pharmacology & Therapeutics 15(2):111–117, 1974). For example, such literature teaches that the presence of fever conditions generally tend to decrease the formation of σ-hydroxyhippuric acid. Liver disease, however, generally does not produce any change in excretion of σ-hydroxyhippuric acid. On the other hand musculoskeletal trauma and abdominal operations are thought to increase the output of σ-hydroxyhippuric acid. Increased excretion of σ-hydroxyhippuric acid also has been noted in patients with anemia and chronic traumatic musculoskeletal trauma. It also has been noted that levodopa and methyl dopa may increase excretion of σ-hydroxyhippuric acid. Uremic patients show increased levels in serum and dialysis fluid. Some of the more detailed and documented observations thus far made in the literature concerning σ-hydroxyhippuric acid/disease relationships are as follows:

Fever

It has been found that formation of σ-hydroxyhippuric acid from salicylic acid is much decreased in febrile patients (Kapp, E. M., and Coburn, A. F.: Urinary metabolites of sodium salicylate. J. Biol. Chem., 145:549–565, 1942).

Trauma

Abdominal operations have been found to be followed by increased urinary output of σ-hydroxyhippuric acid as well as hippuric acid (Szumiel, I., Chmielewska, I., and Manicki, J.: N-substituted peptides in urine in the postoperative period, Bull. Acad. Pol. Sci. (Biol) 13; 565–567, 1965). Again, the urines of patients with severe musculoskeletal trauma were discovered to contain increased amounts of this material from endogenous sources. This increase was particularly striking in patients with poor wound healing. In this connection it is interesting to note that salicylates are generally thought to retard wound healing. However, there are no corresponding data on any such possible effect from σa-hydroxyhippuric acid. However, the existence of large amounts of σ-hydroxyhippuric acid suggests the presence of its precursor, salicylic acid. It also had been shown that salicyluric acid, when administered, is partly hydrolyzed to salicylate.

The finding of increased endogenous production of σ-hydroxyhippuric acid in patients after trauma also suggested that increased activity of the tyrosine-dopa-catecholamine pathway may be measured by studying the urinary excretion of the compound. In fact, this increased excretion may explain the mysterious failure of patients with severe chronic trauma to excrete increased amounts of catecholamines and valine mandelic acid ("VMA") derivatives in the urine. In effect, the compound may indicate a second alternate pathway in catecholamine metabolism (the other being the indole pathway).

Anemia of Trauma

Patients with chronic traumatic musculoskeletal lesions have an agenerative-hemolytic anemia that has not yet been fully characterized. Among other things, such patients are known to lose excessive amounts of iron and copper in their urine, a fact of great interest with respect to their increased output of σ-hydroxyhippuric acid, a substance known to chelate metals. However these patients are also known to excrete other metal-chelating compounds in their urine.

Liver Diseases

The decreased hippuric acid formation and excretion that occur in patients with extensive parenchymatous liver disease has naturally led to a study of σ-hydroxyhippuric acid formation and excretion in such patients. The amount of the compound excreted after the ingestion of aspirin by such patients is normal or low. In dogs with portocaval shunts, a decreased amount of salicyluric acid is excreted in the urine.

Hypertension

The excretion of σ-hydroxyhippuric acid is usually normal in patients with hypertension but may be slightly increased or decreased in some of them.

Levodopa and Methyldopa

Giving methyldopa to female albino rats caused increased urinary output of σ-hydroxyhippuric acid; however, administration of the drug in therapeutic doses to a woman and to a man did not have this effect. It should also be noted that in other studies on urine samples taken from patients who were receiving levodopa for parkinsonism, a majority were found to contain large amounts of compounds with the chromatographic and fluorescence properties of σ-hydroxyhippuric acid and related compounds (Altschule, M.D., and Hegedus, Z. L., σ-hydroxyhippuric (salicyluric) acid—its physiologic and clinical 10 significance; Clinical Pharmacology and Therapeutics, 15: (2) 111–117, 1974).

Down's Syndrome

Children with Down's syndrome have an abnormality of salicylate metabolism. Following the ingestion of aspirin there is an abnormally large amount of it bound in the red blood cells, and a much lower concentration in the plasma. Their urinary output of σ-hydroxyhippuric acid is abnormally low after they ingest aspirin.

Uremia

Increased amounts of hippuric acid are found in the body fluids of patients with renal insufficiency. Increased amounts also are found in their serum and also in their dialysis fluid. It has been postulated that its increased concentration might be responsible for some of the manifestations of uremia. Whether or not this conclusion is valid remains to be seen. However, the removal of considerable amounts of the compound via dialysis raises the interesting possibility that by binding iron, the compound carries off enough iron to explain the mysterious iron loss of dialysis.

Pheochromocytoma

Patients with pheochromocytoma are known to excrete large amounts of catecholamines but only normal amounts of σ-hydroxyhippuric acid.

Thus, it would seem fair to say that the literature does not appear to teach or even suggest that the presence of σ-hydroxyhippuric acid may be used to diagnose the presence of appendicitis. Obviously, given the fact that the diagnosis of appendicitis is now made on clinical grounds alone, and given the high false positive experience inherent in the prior art's forced reliance on clinical grounds alone, a chemical test, and especially a chemical test with both a high sensitivity and a high specificity, would be of extreme value to the diagnostician.

SUMMARY OF THE INVENTION

The methods of this patent disclosure are based upon applicant's qualitative and quantitative findings regarding the presence of and concentrations of σ-hydroxyhippuric acid in the urine and/or blood of human beings suffering from appendicitis. For example, the threshold concentration of σ-hydroxyhippuric acid (also commonly designated to as orthohydroxyhippuric acid and hereinafter often designated as "OHHA") in the urine of human beings suffering from appendicitis is at least about 10 mg/L (10 mg/liter). A reading of less than about 10 mg/L is indicative of the probable absence of appendicitis in such a person. Such concentrations can be measured by various quantitative, semi-quantitative or qualitative chemical techniques known to the chemical arts. Color-producing chemical reactions, thin layer chromatography ("TLC"), high pressure liquid chromatography ("HPLC"), fluorescence spectroscopy, ultraviolet (UV) visible light absorbance spectroscopy, mass spectroscopy and gas chromatography (GC) mass spectroscopy techniques are especially preferred techniques for the practice of this invention. It should also be emphasized that the 10 mg/L σ-hydroxyhippuric acid concentration/appendicitis correlation has been clinically tested and has been proven to be valid.

This 10 mg/L concentration may be measured in a raw urine sample, or in an OHHA sample extracted from a raw urine sample, or it may be the subject of an empirical correlation between the amount of OHHA extracted from a urine sample and the presence of the 10 mg/L or more concentration in the urine sample. Here again, OHHA concentration less than about 10 mg/L is indicative of the absence of appendicitis. In some particularly preferred embodiments of this invention raw urine is subjected to color reaction-producing tests. In some other particularly preferred embodiments, OHHA is extracted from a raw urine sample, subjected to thin layer chromatography tests and then subject to various color developing procedures such as the use of color developing reagents or the use of UV light to note certain color spots indicative of the presence of OHHA in a given concentration. In some particularly preferred embodiments of this invention, empirical indications of the 10 mg/L OHHA concentration in the original urine sample will be the appearance of a blue fluorescent spot on a TLC plate, which is visible to the eye under an ultraviolet light source at 250 to 360 nm. The production of a colored spot produced when σ-hydroxyhippuric acid is reacted with various color reaction producing ions such as those of $Fe^{+++}$ and $Cu^{+++}$ can also be the basis of such an empirical indication of appendicitis.

In effect, this visualizing procedure in this wavelength range and/or color reaction test will reveal whether or not a colored spot with a retention factor (rf) comparable to a known pure standard of σ-hydroxyhippuric acid can be detected. In any event, the presence of such a spot is an especially useful empirical indicator of the presence of σ-hydroxyhippuric acid in human urine at a concentration of at least 10 mg/L. Conversely, the absence of such a spot is indicative of the absence of appendicitis.

The results of a quicker, but less specific screening, color reaction test also may be employed to show a correlation with the presence of appendicitis. In some of the most preferred embodiments of applicant's process, this color reaction test is first employed as a preliminary "screening" test which can be followed by one or more exact versions of applicants more specific tests. The procedures associated with this preliminary screening are shown as Part A (or Procedure A) of FIG. 1. It should also be noted that the absence of such a color reaction is also, in its own right, a very useful "negative indicator" of appendicitis. This screening test can be, and preferably is, followed by a more specific and sensitive test based upon TLC techniques. This procedure is shown as Part B (or Procedure B) of FIG. 2. Preferably an overall test employing Parts A and B will be employed to give maximum confidence in this overall (A+B) test.

Other methods by which the presence of σ-hydroxyhippuric acid, at or above about a 10 mg/L threshold concentration, may be confirmed would include a wide variety of other qualitative and quantitative chemical identification techniques known to the art. They can be used as a single step test or in conjunction with each other a la applicant's Part A (color reaction), Part B (TLC) overall test. For example, such identification techniques could be selected from the group of chemical techniques consisting of: High Pressure Liquid Chromatography ("HPLC"), Mass Spectrometry ("MS"), High Resolution Mass Spectrometry ("HRMS"), Gas Chromatography Mass Spectrometry ("GCMS"), Nuclear Magnetic Resonance Spectrometry ("NMR"), Ultraviolet Absorbance Light Spectroscopy ("UV"), Fluorescence Spectroscopy, Infrared Spectroscopy ("IR"), Spectrophotometric Colorimetry, Color Chart Comparison, Monoclonal Antibody Tests, Radioimmunoassay Tests, Enzymatic Tests, and Electrophoresis.

Stated in patent process and patent apparatus terminology, some of the more preferred embodiments of this invention can be described various ways, for example:

1. A method for diagnosing appendicitis, said method comprising:

obtaining a urine sample from a human being suspected of having appendicitis; and determining that the concentration of σ-hydroxyhippuric acid in the urine sample is at least about 10 mg/liter and thereby indicating the probable presence of appendicitis in said human being.

2. A method for diagnosing appendicitis, said method comprising:

obtaining a urine sample from a human being suspected of having appendicitis by virtue of nausea, vomiting or anorexia in association with abdominal pain, which is characteristically present in the periumbilical or right lower quadrant area; and determining that the concentration of σ-hydroxyhippuric acid in the urine sample is at least about 10 mg/liter and thereby indicating the probable presence of appendicitis in said human being.

3. A method for diagnosing appendicitis, said method comprising:

obtaining a urine sample from a human being suspected of having appendicitis by virtue of nausea, vomiting or anorexia in association with abdominal pain, which is characteristically present in the periumbilical or right lower quadrant area; and chemically extracting an σ-hydroxyhippuric acid component from the urine sample; and determining by a color-producing chemical reaction of the σ-hydroxyhippuric acid component that the concentration of σ-hydroxyhippuric acid in the urine sample was at least about 10 mg/liter and thereby indicating the probable presence of appendicitis in said human being.

4. A method for diagnosing appendicitis, said method comprising:

obtaining a urine sample from a human being suspected of having appendicitis by virtue of nausea, vomiting or anorexia in association with abdominal pain, which is characteristically present in the periumbilical or right lower quadrant area; and determining by a color producing chemical reaction based upon use of ferric ion that the concentration of σ-hydroxyhippuric acid in the urine sample is at least about 10 mg/liter and thereby indicating the probable presence of appendicitis in said human being.

5. A method for diagnosing appendicitis, said method comprising:

obtaining a urine sample from a human being suspected of having appendicitis by virtue of nausea, vomiting or anorexia in association with abdominal pain, which is characteristically present in the periumbilical or right lower quadrant area;

chemically extracting an σ-hydroxyhippuric acid component from the urine sample using a chemical extraction system based upon the use of σ-hydroxyhippuric acid— extracting compounds selected from the group consisting of ferric ion, diethylether, butanol, a C18 bonded silica used to place the σ-hydroxyhippuric acid component in an aqueous environment or a C18 bond silica used to place the σ-hydroxyhippuric acid component in a methanol environment in order to prepare the σ-hydroxyhippuric acid component to undergo a color reaction; and determining that the concentration of σ-hydroxyhippuric acid originally in the urine sample was at least 10 mg/liter by subjecting said σ-hydroxyhippuric acid component to thin layer chromatography and then noting, with the aid of ultraviolet light having a wave length from about 250 nm to about 360 nm, the presence of a blue fluorescent spot with a retention factor equal to a reference standard based upon known concentrations of σ-hydroxyhippuric acid and thereby indicating the probable presence of appendicitis in said human being.

6. A method for diagnosing appendicitis, said method comprising:

obtaining a urine sample from a human being suspected of having appendicitis;

performing a first test by reacting a σ-hydroxyhippuric acid component of a first portion of the urine sample with a ferric silica material to produce a color reaction;

performing a second test by: (b 1) extracting an σ-hydroxyhippuric acid component from a second portion of the urine sample, (2) subjecting the σ-hydroxyhippuric acid component to thin layer chromatography, (3)

developing a colored spot on a thin layer chromatography film and (4) comparing the colored spot to a control color chart to determine that the concentration of σ-hydroxyhippuric acid in the urine sample is at least about 10 mg/L and thereby indicating the probably presence of appendicitis in said human being.

7. A kit for diagnosing appendicitis, said kit comprising: chemical means for reacting σ-hydroxyhippuric acid in human urine to produce a color reaction and means for determining that the concentration of the σ-hydroxyhippuric acid in the human urine is at least about 10 mg/liter and thereby indicating the probable presence of appendicitis in said human being.

8. A kit for determining the presence of σ-hydroxyhippuric acid in human urine in a concentration of at least 10 mg/liter, said kit comprising:

a vial containing a reagent capable of undergoing a color-producing reaction with σ-hydroxyhippuric acid;

means for adding a measured amount of urine to the reagent in order to produce a color reaction; and a color comparison chart to which a product of the color reaction is compared.

9. A kit for determining the presence of σ-hydroxyhippuric acid in human urine in a concentration of at least 10 mg/L, said kit comprising:

a vial containing a chemical capable of undergoing a color-producing reaction with an σ-hydroxyhippuric acid component of the human urine;

a chemical reagent capable of extracting an σ-hydroxyhippuric acid component of the human urine;

thin layer chromatography means for acting upon the σ-hydroxyhippuric acid component;

thin layer chromatography means for developing a colored spot on the thin layer chromatography means; and color chart means for comparing the colored spot to said color chart means to determine that the concentration of σ-hydroxyhippuric acid in the urine is at least about 10 mg/L and thereby indicating the probable presence of appendicitis in said human being.

10. A kit for determining the presence of σ-hydroxyhippuric acid in human urine in a concentration of at least 10 mg/liter, said kit comprising:

a vial containing a ferric silica reagent to which a first measured amount of urine is added;

means for adding a measured amount of urine to the ferric silica reagent;

a color comparison chart;

a syringe containing a citrate buffer to receive a measured amount of a second measured amount of a urine sample;

an extraction cartridge containing a C18 reagent and having means for receiving a fluid discharge from the syringe;

a vial of water for passing said water through the extraction cartridge containing the C18 reagent after the discharge from the syringe is passed through said extraction cartridge;

a vial of a solvent capable of extracting σ-hydroxyhippuric from the C18 contained in the extraction cartridge;

a sample collection vial used to collect a solvent/σ-hydroxyhippuric acid sample from the extraction cartridge;

a tank for holding the solvent/σ-hydroxyhippuric acid sample;

a holder mounted thin layer chromatography plate having a first plate area designated to receive a sample of the solvent/σ-hydroxyhippuric acid sample and a window area to receive a discharge from a swab impregnated with the solvent/σ-hydroxyhippuric acid and dispensing at least a portion of said sample on the window area of said plate;

a swab; and a control standard means of comparing positions of spots which appear in the window area of the plate with the said control standard means.

11. A method for diagnosing the absence of appendicitis, said method comprising:

obtaining a urine sample from a human being 10 suspected of having appendicitis; and determining that the concentration of σ-hydroxyhippuric acid in the urine sample is less than about 10 mg/liter and thereby indicating the probable absence of appendicitis in said human being.

12. A kit for diagnosing the absence of appendicitis, said kit comprising: chemical means for reacting σ-hydroxyhippuric acid in human urine to produce a color reaction and means for determining that the concentration of the σ-hydroxyhippuric acid in the human urine is less than about 10 mg/liter and thereby indicating the probably absence of appendicitis in said human being.

DESCRIPTION OF PREFERRED EMBODIMENTS

The general teachings of this patent disclosure have many preferred embodiments. Some of these preferred embodiments revolve around applicant's findings regarding the 10 mg/L "threshold concentration" of σ-hydroxyhippuric acid as being indicative of the presence of appendicitis in humans. Conversely, readings of less than about 10 mg/L are indicative of the absence of appendicitis. Some preferred embodiments of this invention also involve the use of certain specific test procedures to establish the existence of this 10 mg/L concentration. Other preferred embodiments are more concerned with the use of certain apparatus (e.g., test kits) which are especially well suited for quickly carrying out some of the certain chemical procedures.

We can begin this discussion concerning the more preferred embodiments of this invention by first noting that the 10 mg/L concentration was established empirically. That is to say that this concentration was derived from actual patient data obtained from several clinical studies. However, it also should be noted that some generalizations had to be made with respect to the "placement" of applicant's "threshold" concentration at the 10 mg/L level which is employed to establish this invention. For example, when applicant observed a positive Part A in certain hereinafter described tests having both a Part A and Part B, the Part A (screening test) often corresponded to a OHHA concentration of above about 20 mg/L. However, in looking at certain color charts prepared for comparison purposes, e.g., that employed in Part A of the two part (i.e., Part A and Part B) test, it was not always easy to differentiate "normal" OHHA concentrations from those above about 10 mg/L to about 20 mg/L. On the other hand, applicant's TLC method proved to be much more sensitive in that it more accurately differentiated interfering substances from OHHA. The levels detected by TLC tests were more clearly established at 10 mg/L and above. On the other hand, when applicant used HPLC methods, it was possible to quantitate virtually any concentration level, but applicant eventually chose to use a 10 mg/L concentration as being indicative of the presence of appendicitis in patients using this particular test techniques. After a great deal of trial work with these various techniques, applicant determined that, all things considered a 10 mg/L σ-hydroxyhippuric acid concentration served as the best "threshold" level for the prediction of appendicitis. This concentration is a particularly useful one when applicant's color reaction and TLC procedures are employed. The fluorescence, UV/Visual spectroscopy, mass spec troscopy and GC/mass spectroscopy are less preferred and, in general, will be better employed in conjunction with other test techniques. For example, applicant found that fluorescence and UV/Visual spectroscopy were especially useful as detection means when they were used in conjunction with HPLC. Fluorescence, however, can be especially useful in Part B of applicant's two part (Part A and Part B) test. Among other things, the virtue of this procedure is that it does not stain the TLC plate. However, the sensitivity of this method is often "too high" (i.e., it detects OHHA levels down to about 5 mg/L).

It also should be emphasized at this point that the sensitivity of the herein described methods can be adjusted to pick up applicant's "threshold" 10 mg/L OHHA concentration by applying less (or more, as the case may be) volume of the extracted urine to the TLC plate. For example, applicant's test kit can utilize its Part A and its Part B in a manner such that about 10 mg/L is the designed sensitivity "threshold" in each part.

It also should be noted in passing that certain hereinafter described "blue spot" tests were based upon the use of a fluorescent spot which will appear prior to any staining the TLC plate. In many cases, the blue spot test is more sensitive than the staining test of the TLC plate, i.e., a lower OHHA level (e.g., 7 mg/L) can be detected by this method when using, for example, 5 applications on a plate However, after staining the plate with a coloring solution one might not see this spot under a fluorescent light. Applicant also generally found that this spot has to be an intense blue spot in order to well correlate with the presence of appendicitis. At any rate, such a plate can readily be pre-spotted with a standard solution that corresponds to a 10 mg/L concentration level.

The preparation of applicant's color chart was carried out by methods well known to this art. For example, various standard concentrations of OHHA, in "normal" urines, were made as references. Final concentration samples of :0, 2.5, 5, 10, 20, 30, 50, 100, 200, 500, 1000 mg/L were then prepared. The colors formed by the reactions occurring in these samples were then photographed and used as the basis of color chart systems. Such charts were accordingly marked for "positives" at about a 10 mg/L concentration and for "negatives" at about :0, 2.5 and 5 mg/L concentrations.

Some variation in these test procedures is possible. By way of example, in Part A of applicant's two part (Part A and Part B) test, the absence of color can be taken to correlate with the absence of appendicitis. However, a positive result could be related to the presence of other phenolic compounds in the patient's urine. Hence, applicant thought it prudent to develop a Part B to provide a more certain test. That is to say that Part B is more specific and can more accurately identify whether or not a positive result in Part A is truly caused by OHHA, or by an interfering substance. In other words, embodiments of this invention double or "verification" tests are contemplated. For example, in applicant's preferred "two stage" test, Part B test is much more specific for OHHA than the Part A test. In other words, in this Part A/Part B version of applicant's invention, the absence of OHHA in Part B of applicant's test can be taken as being indicative of the absence of appendicitis.

However, those skilled in this art also will appreciate that no chemical/biological test will always perform "perfectly" and applicant's test for a 10 mg/L OHHA concentration/ appendicitis disease state is no exception. However, the specificity of applicant's test, which is a measure of how well one can detect the negatives, is above 90% and this level of reliability is extremely useful to a diagnostician struggling to differentiate appendicitis from a host of other disease possibilities.

CLINICAL STUDIES

The efficacy of the herein described methods and apparatus for detecting appendicitis were subjected to extensive clinical testing. The general nature and scope of these clinical tests will be described. However, before going into such matters it should be noted that pathology reports of surgical specimens were the basis used to confirm the presence or absence of appendicitis. For example, in Table 4 of this patent disclosure, the "+surgery" notation means a positive pathology report for appendicitis was obtained for a patient who underwent surgery. Criteria for a positive pathology report are well established. They generally consist of macroscopic and microscopic findings. For example, the appearance of a reddened, swollen, friable to the touch, appendix, surrounded by either a serous or purulent exudate are classic macroscopic signs of appendicitis. Even more accurate microscopic findings will consist of findings of inflammatory changes (presence of neutrophils, monocytes, etc.) in the appendiceal mucosa, wall or lumen. Consequently, applicant's definition of "+surgery" was a positive pathology report on an appendix surgical specimen as per a pathologist's interpretation of such evidence.

1.1 Clinical Investigation Methods and Clinical Protocols

Random, convenient urine samples were obtained from patients over a one year period. Samples were obtained from selected patients with complaints of abdominal pain and suspected of having appendicitis. Their urine samples were tested retrospectively and reviewed against surgical or discharge diagnosis. The study of applicant's methods to assess the presence of the marker of interest (OHHA) without knowledge of the diagnosis of the individual patient. Likewise, the results of applicant's tests were not available to the clinician treating the patients. Therefore, decisions to bring patients to the operating room were in no way influenced by the results provided by applicant's testing methods. Moreover, the operational diagnosis of acute appendicitis was limited to the results of surgical pathology. Patients who were not taken to the operating room were considered to have no appendical pathology.

1.2 Number of investigators and subjects per investigation.

Between March 1989 and March 1990, 220 random, convenient samples were obtained from patients arriving at the emergency departments of two different hospitals: Swedish Medical Center, Englewood, Colo. and Lutheran Medical Center, Denver, Colo., with abdominal pain which at least suggested the presence of appendicitis. The patient population was comprised of 83 males (37.7%) and 137 females (62.3%). Patient information was at that time limited to patient sex and diagnosis. The study represented a validation study and strict criteria were reserved for future investigation.

1.3 Subject selection and exclusion criteria.

In these studies, the inclusion criteria for the 220 patients were: (1) patients were male and female patients of all ages, (2) patients presented to the study were required to be presented with a history of acute abdominal pain of any type, with or without localization of no more than 72 hours duration, (3) patients so presented were also presented with or without nausea, vomiting, fever or other systemic symptoms and (4) patients who were presented with abdominal signs indicating a surgical pathology on physical examination, but who did not have abdominal pain, were included—provided that appendicitis was a reasonable part of the diagnostic evidence. The "exclusion criteria" were centered upon whether or not the patient had taken salicylates or antibiotics within the 24 hours period preceding the taking of the patient's urine sample.

1.4 Results of statistical analysis of the clinical investigation.

One hundred twenty-two patients (55%) went to surgery based on a clinical diagnosis of acute appendicitis. Eighty-six (70.5%) of these had histopathologically confirmed appendicitis. Applicant's test was positive in 82 (67.2%). Of the 98 cases that did not go to surgery, there were five false positive tests.

The test results and diagnosis for those who went to surgery are tabulated in TABLE 1 below:

TABLE 1

| TEST | APPENDICITIS + | APPENDICITIS − | |
|---|---|---|---|
| + | 79 | 3 | 82 |
| − | 7 | 33 | 40 |
| | 86 | 36 | 122 |
| PRE-TEST PROBABILITY | | | 70.5% |

The test statistics (based on the above 2 × 2 table) are:

| | | $CI_{95}$ |
|---|---|---|
| SENSITIVITY | 91.86% | 83.9, 96.7 |
| SPECIFICITY | 91.67% | 77.5, 98.2 |
| POSITIVE PREDICTIVE VALUE | 96.34% | 89.7, 99.2 |
| NEGATIVE PREDICTIVE VALUE | 82.50% | 67.2, 92.7 |

Of the 98 cases that did not go to surgery there were five false positives (5.1%). Of the 220 patients included in the study, 122 had an operative procedure (55.4%) and 86 (39.1%) were diagnosed with appendicitis. The test was positive in 87 cases (39.5%) and negative in 133 (60.5%).

TEST STATISTICS

The test performance is shown in the 2×2 table:

TABLE 2

| TEST | APPENDICITIS + | APPENDICITIS − | |
|---|---|---|---|
| + | 79 | 8 | 87 |
| − | 7 | 126 | 133 |
| | 86 | 134 | 220 |

TABLE 2-continued

The Pre-Test Probability (Prevalence of appendicitis in the sample) was 39.1%

The test statistics (based on the above 2 × 2 table) are:

| | | $CI_{95}$ |
|---|---|---|
| SENSITIVITY | 91.86% | 83.9, 96.7 |
| SPECIFICITY | 94.03% | 88.6, 97.4 |
| POSITIVE PREDICTIVE VALUE | 90.80% | 82.7, 95.9 |
| NEGATIVE PREDICTIVE VALUE | 94.74% | 89.5, 97.9 |

LABORATORY STUDIES

Some of the more preferred embodiments of the chemical tests which can be used to establish the presence of the 10 mg/L OHHA concentration in a patient's urine were established by the following laboratory studies.

A Preferred Method For The Detection Of σ-Hydroxyhippuric Acid In Direct Urine Using Ionically Bonded Ferric Silica A particularly effective method for the improvement of a ferric ion color reaction was developed as a result of certain laboratory studies. It utilizes the acidic nature of the surface of a silica gel. It also should be noted that the sensitivity and selectivity and intensity of this color reaction can to some extent be controlled by the pH, solution media and the concentration of the ferric ion in solution. To this end, a fixing of the ferric ion to the surface of the silica and use of the silica to add acidity to the urine sample was employed. The resulting material may be used as a free flowing powder or coated onto a solid material backing and used for test strips or papers. Applicant also found that other support materials—other than silica—also may be used; these include: Celite®, clays, alumina and/or fire brick.

A Preferred Method For The Preparation Of A Ferric Bonded Silica

Forty grams of ferric nitrate hexahydrate was dissolved in 40 ml of 25% hydrochloric acid and sonicated for 15 minutes. Then 100 g of silica was slowly stirred into the ferric nitrate solution until a free flowing powder was obtained. The treatment of the silica surface with hydrochloric acid, before adding the ferric nitrate activates the surface hydroxyls to ionicly attach to the ferric groups.

A Preferred Method For The Detection σ-Hydroxyhippuric Acid In Direct Urine

For the purpose of this test the urine obtained from patients suspected of having appendicitis was used directly, i.e., the σ-hydroxyhippuric acid was not extracted prior to this test.

Reagent- 100 mg of ferric bonded silica in a 1 ml vial

Method of Detection- Color observation

Procedure

Add approximately 200 ul (microliter) of urine to a 1 ml amount of ferric bonded silica in a vial. The vial was shaken and allowed to settle for two minutes.

Results

A color change in the top layer of liquid from a normal urine light yellow to a pink, red, or violet color indicates a high level of phenolics and in particular σ-hydroxyhippuric acid which can be indicative, in its own right, of appendicitis. More importantly in this non-specific method, no color change usually indicates negative appendicitis. This color change is best employed by comparing its result with either a color comparison chart or when run along with positive and negative markers.

Again, those skilled in the art will appreciate that many other tests may be employed to detect the minimal presence of and, if need be, a more exact concentration of σ-hydroxyhippuric acid in urine. Again, the more preferred techniques are color reaction-producing tests, high pressure liquid chromatography ("HPLC") and thin layer chromatography ("TLC") tests. Other tests, e.g., gas chromatography ("GC") and other chromatographic techniques as well as ultraviolet ("UV"), infrared ("IR"), visible spectroscopy, nuclear magnetic resonance ("NMR"), mass spectrometry, GC/mass spectrometry, specific impregnated test papers, monoclonal antibody, radioimmunoassay enzyme, electrophoresis and/or combinations of any of these techniques may be employed to detect the minimal σ-hydroxyhippuric acid concentration (i.e., at or above about 10 mg/L) which correlates with the presence of appendicitis.

Of these tests, liquid chromatography methods (e.g., HPLC and TLC) are the more preferred to obtain the most accurate and selective measurement of the σ-hydroxyhippuric acid concentrations. From the more "practical" point of view, applicant's color reaction 10 tests such as those achieved through the use of reactions of ferric ion and OHHA are highly preferred. It also should be noted that light spectrophotometric and color change methods generally give a faster, but less selective, determination compared to say HPLC and/or TLC.

The finer details of some of the preferred specific methods by which the σ-hydroxyhippuric acid component of urine samples were identified and quantified, together with some representative examples of techniques with respect to certain possible analytical methods which were used to further establish this invention, were as follows:

Solid Phase Extraction

Applicant found that, since the σ-hydroxyhippuric acid component of the urine samples is in solution with a complex matrix of proteins, salts and other compounds normally contained in urine, it sometimes is advantageous to chemically extract the targeted compound with the minimum amount of contaminants. Although a conventional solvent extraction procedure using chemical systems such as diethylether or butanol, with various pH adjustments gives excellent recoveries, the use of a simplified solid phase extraction generally is quicker and cleaner. Two examples of such chemical extraction are presented here; both employ a C18 bonded silica; example (A) given below leaves the σ-hydroxy-hippuric acid component in an aqueous environment, whereas example (B) supports the σa-hydroxyhippuric acid in a methanol environment. Either extraction procedure can be used depending on the desired support media needed for a secondary analysis stage. Other bonded phases such as shorter alkyl side chains were examined, as were phases to utilize ion exchange capabilities such as $NH_2$, CN and other groups with generally equal success using slightly differing eluting solvents known to the art.

EXAMPLE A

Urine Extraction into Aqueous Solvent

As weak acids, phenols form salts with sodium and other alkali metals very easily at a pH 2 or 3 units above its pKa. These salts are very water-soluble, so much in fact that they are not retained by a column filled with a C18 bonded silica. Therefore ionization was suppressed by buffering the urine to at least 2 to 3 pH units below its pKa. This done, the compound will then be retained by the column.

Understanding this phenomenon, the following extraction procedure was then devised:

1) A C18 bonded silica disposable extraction tube containing 100 mg of material was used.

2) The column was washed with 1 ml of methanol followed by 1 ml of water.

3) A 1 ml sample of urine was acidified with either 100 μl of concentrated HCl or 100 mg of citric acid or the addition of an ion exchange resin and allowed to stand for about two minutes. The acidified urine was then passed through the previously conditioned 1 ml C18 extraction tube.

4) The tube was then washed with 1 ml of water and the washings discarded.

5) The material was eluted with 1 ml of sodium acetate buffer 0.05M pH 6.0 (any other buffers with a pH above 5.5 can be used).

The elution fluid is colorless to the eye and the yellow or brown urine pigments remain on the column so as not to contaminate the eluent.

When tested for recovery, the levels are satisfactory and typical example values are shown below.

Recovery of σ-hydroxyhippuric acid is shown in Table 3:

TABLE 3

| Elution Volume | % Recovery | Total % Recovery |
|---|---|---|
| 1 ml | 47.0% | 47.0% |
| 2 ml | 24.6% | 71.6% |
| 3 ml | 10.7% | 82.3% |
| 4 ml | 6.5% | 88.8% |

Note: Use of a different buffer pH or concentration seems to have little effect on recovery.

EXAMPLE B

Urine Extraction into Methanol

Using a non-polar extraction procedure and considering that phenols are weak acids, ionization was suppressed by buffering the urine to at least 2 to 3 pH units below its pKa. The compound will then be retained by a column filled with a C18 bonded silica.

Understanding this phenomenon, the following extraction procedure was devised:

1) A C18 bonded silica disposable extraction tube containing 100 mg of this material was used.

2) The column was washed with 1 ml of methanol followed by 1 ml of water.

3) A 1 ml urine sample was acidified with either 100 μl of concentrated HCl or 100 mg of citric acid or the addition of an ion exchange resin and allowed to stand for about two minutes. The acidified urine was then passed through the previously conditioned 1 ml C18 extraction tube.

4) The tube was then washed with 1 ml of water and the washings discarded.

5) The material was eluted with 1 ml of methanol.

The eluted fluid color ranges from colorless to a yellow or brown. Some of the urine pigments are removed from the column during this process. When tested for σ-hydroxyhippuric acid the recovery levels range from 95% to 100%. It should also be noted in passing that the urine samples are preferably fresh and are preferably used before refrigeration. It should also be noted that blood samples could also be used in place of, or in addition to, urine samples.

Thin Layer Chromatography

Thin layer chromatography is probably the easiest qualitative chromatographic method of identifying threshold levels of σ-hydroxyhippuric acid in the urine of patients suspected of having appendicitis. Thin layer silica plates supported on either glass, metal or plastic backing, preferably without any fluorescent indicator, were normally used although paper and silica impregnated paper gave similar results.

Method

From 1 to 5 μl of a methanol extract of a urine sample, obtained using extraction method (B) previously described, was spotted on to the surface of the plate. The plate was then developed using an ascending technique with a mobile phase eluting solvent comprised of one part glacial acetic acid with 99 parts of ethyl acetate.

Detection was done by either of two methods:

a) by use of 250 to 350 nm ultraviolet light which produces a blue fluorescing spot; or b) by spraying or dipping the plate in a solution of ferric nitrate in methanol to develop a red spot.

Results

The results of TLC under these conditions revealed a spot with a retention factor (Rf) of approximately 0.4 for σ-hydroxyhippuric acid and 0.6 for salicylic acid. Plates were always run with a standard of pure σ-hydroxyhippuric acid to allow for any minor changes in the mobile phase or silica composition. This particular solvent system is especially efficacious in separating hippuric acid, σ-hydroxyhippuric acid and salicylic acid. Other systems were used to separate other possible contaminants.

HPLC Analysis

High pressure liquid chromatography is another highly preferred quantitative chromatographic method for identifying the "threshold" (10 mg/L) levels of σ-hydroxy-hippuric acid in the urine of patients suspected of having appendicitis.

Urine samples, preferably fresh and preferably unrefrigerated, were normally employed, although blood samples could also be similarly employed. It also should be noted in passing that this technique is quantitative and some patients have been shown to have OHHA levels in excess of 2 g/L, a lowering of the temperature of a stored urine to below 4° C. can cause samples with high concentrations of σ-hydroxyhippuric acid to precipitate out of solution therefore giving reduced values.

Those skilled in this art will also appreciate that the use of differing detection methods may greatly enhance the sensitivity and selectivity of a given analysis. To further examine these points, applicant has reviewed the findings of this patent disclosure with respect to specific wavelength monitoring, fluorescence, electrochemical and mass detection.

Method

Five to 25 μl of an extract of a urine sample obtained using either of the extraction methods previously described was injected into an HPLC system running under the following conditions:

Solvent: 50 % methanol 50% phosphate buffer 0.01M at pH 2.3

Flow Rate: 1 ml/min.

Column: C18 Apex octadecyl

Size: 5μ 15 cm×4.5 mm i.d.

Temperature: 20° C.

Detector: UV at 236 and/or 300 nm.

Results of HPLC analysis were quantified using multipoint calibration and a good straight line fit was obtained over a 1 to 2000 mg/L σ-hydroxyhippuric acid concentration range. Under these conditions a peak was revealed with a retention time of about 3.0 minutes with an absorbance spectra consistent with σ-hydroxyhippuric acid. Adequate separation is achieved between all the likely interfering compounds e.g., hippuric acid, salicylic acid and various other phenolic compounds. This is required to reduce false elevated values due to salicylate ingestion. All identification of compounds and retention times were checked using pure known standards.

Color Reaction with Direct Urine

For the purpose of this test the urine obtained from patients suspected of having appendicitis was used directly and not extracted prior to carrying out this test.

Reagent: 3M solution of hydrated ferric nitrate in 3M hydrochloric acid in water.

Detection: UV-VIS spectrophotometer Hitachi U2000 and color observation.

Method

To 1 ml of urine 0.1 ml of the reagent is added and the visual color change observed. For evaluation purposes absorbance measurements were taken by scanning from 400 to 900 nm and the following semi-quantitative estimations were calculated after allowing for a normal urine blank. If absorbance readings were greater than 2.0 then the urine sample was diluted 1 part urine to 10 parts water and the corresponding factor applied to the calculations. A calibration curve was constructed by adding known amounts of σ-hydroxyhippuric acid to normal urines and was found to be linear up to 300 mg/L. To the same standards a quantity of reagent was added to produce a set of standards for color comparison. The results of such tests were photographed and used as a part of a color chart used as a standard of comparison for samples actually tested for the threshold levels of σ-hydroxyhippuric acid.

Results

As this is a non-specific method a wide range of differences are noted from the HPLC estimations and the direct urine calculations. The values are much larger by this method because all the reactive materials combine to give a total estimation. Even so there is still a good correlation from the strongly elevated urines (greater than 500 mg/L) and a corresponding increase in absorption. These results are summarized in TABLE 4 below.

TABLE 4

| Ref | Dilution Ratio | Abs. 620 nm | Conc. mg/L | Color Change | Surgery |
| --- | --- | --- | --- | --- | --- |
| OHHA | 1:1 | 0.620 | 316 | Yes | |
| NORM | 1:1 | 9.238 | 0 | No | |
| 138 | 10:1 | 0.295 | 1371 | Yes | + |
| 151 | 10:1 | 0.750 | 3671 | Yes | + |
| 143 | 10:1 | 0.667 | 3303 | Yes | + |
| 152 | 1:1 | 0.553 | 159 | Yes | + |
| 187 | 10:1 | 0.272 | 1255 | Yes | + |
| 196 | 1:1 | 1.281 | 527 | Yes | + |
| 136 | 1:1 | 0.456 | 110 | Yes | + |
| 139 | 10:1 | 0.597 | 2898 | Yes | + |
| 197 | 1:1 | 0.815 | 292 | Yes | + |
| 148 | 1:1 | 0.714 | 241 | Yes | + |
| 145 | 1:1 | 0.162 | 0 | No | − |
| 140 | 1:1 | 1.047 | 409 | Yes | − |
| 194 | 1:1 | 0.648 | 207 | Yes | + |
| 142 | 1:1 | 0.346 | 32 | No | − |
| 199 | 1:1 | 0.756 | 262 | Yes | − |
| 147 | 1:1 | 0.211 | 0 | No | − |
| 136/2 | 1:1 | 0.474 | 119 | Yes | + |

Although the measurement of absorption at a specific wavelength is an accurate measurement, the complex nature of the color formation on the many differing components present in the urine leads could lead to inaccuracy. Observation of a color change and then a comparison to standards or a color chart gives a better correlation to the presence of high levels of o-hydroxyhippuric acid. For example, a color change from a normal light yellow urine to a pink, red, or violet color indicates a high level of phenolic compounds which can be indicative of appendicitis. More importantly in this non-specific and purely investigative method, no color change usually was taken to indicate the absence of appendicitis. It also should be noted that with respect to the data at 600 or 620 nm, there is a smooth broad band with no specific lambda maximum, but higher absorbance than background takes place at around 600 nm.

Color Reaction with Extracted Urine

For the purpose of this test the urine obtained from patients suspected of having appendicitis was extracted using extraction method Example B noted previously. The 1 ml sample of methanol was then used for this test.

Reagent: a 2% solution of hydrated ferric nitrate in methanol.

Detection: UV-VIS spectrophoto Hitachi U2000 and color observation photometer.

Method

To 1 ml of the methanol extract of the urine 0.1 ml of the reagent is added and the visual color change observed. For investigative and evaluation purposes, absorbance measurements were taken by scanning from 400 to 900 nm. The following semi-quantitative estimations were calculated after allowing for a normal urine blank. If absorbance readings were greater than 2.0 absorption units, then the urine sample was diluted 1 part urine to 10 parts methanol and the corresponding factor applied to the calculations.

A calibration curve was constructed by diluting a known standard of o-hydroxyhippuric acid and was found to be linear up to 600 mg/L. To the same standards a quantity of reagent was added to produce a set of standards for color comparison. The results of such tests also were photographed and used as relevant parts of a color chart.

Structure Determination and Isolation from Urine of o-Hydroxyhippuric Acid

The observation of a blue fluorescing spot when screening urine samples from patients suspected of having appendicitis using a TLC method was noted. A project to identify and isolate this compound was then carried out. The methods used therein were as follows:

Method

Samples of urine used for isolating the various components were combined from several patients that had confirmed appendicitis and subjected to the following procedures:

1) A C18 bonded silica disposable extraction tube containing 5 g of material was used.
2) The column was washed with 5 ml of methanol followed by 5 ml of water.
3) The urine was passed through the C18 tube.
4) The tube was then washed with 5 ml of water and the washings discarded.
5) The material was eluted with 5 ml of methanol.

The eluted fluid color was yellow to brown. Some of the urine pigments were removed from the column during this process. The methanol solvent was removed under reduced pressure and the crude residue was dissolved in a small amount of methanol and was subsequently analyzed by TLC and HPLC. Further isolation of the blue fluorescent band was carried out first by flash chromatography followed by preparative layer TLC.

Flash Chromatography

Flash silica 20–40 u was packed into a glass tube and conditioned with chloroform and the total crude extract was applied to the top of the bed.

A chloroform/methanol mixture (9:1) was passed through the column using about 200 ml of the solvent to extract all the blue fluorescing material. The extraction process was monitored by TLC and by UV.

Prep TLC

Both TLC and HPLC analysis showed that flash chromatographed fractions were not pure which was only to be expected. However, most of polar components were removed from these extracts. Further purification was achieved by combining fractions containing blue fluorescent compounds and loading on preparative silica TLC plates (6 in number). A solvent system comprising of ethyl acetate 80%; methanol 20%; and 3% acetic acid was used to develop the plates.

The blue components were scraped off the plate and the material was re-extracted into methanol. Filtration followed by solvent removal afforded a crude residue from which white crystals could be precipitated out by adding a few drops of methanol.

Figure 1:
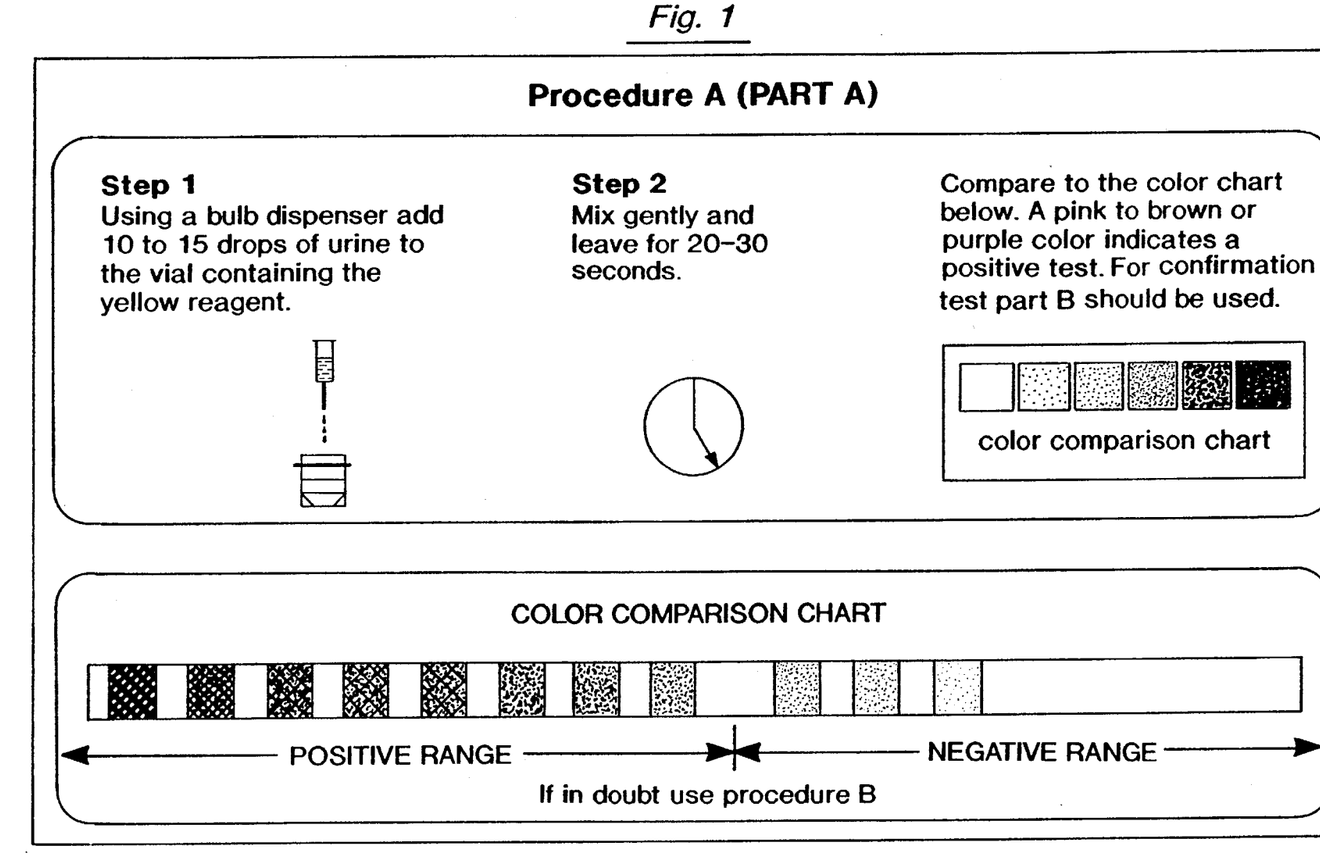
FIG. 1 represents the process steps, apparatus and instructions associated with a "Procedure A" (Part A) of a two part procedure described in this patent disclosure.
Figure 2:
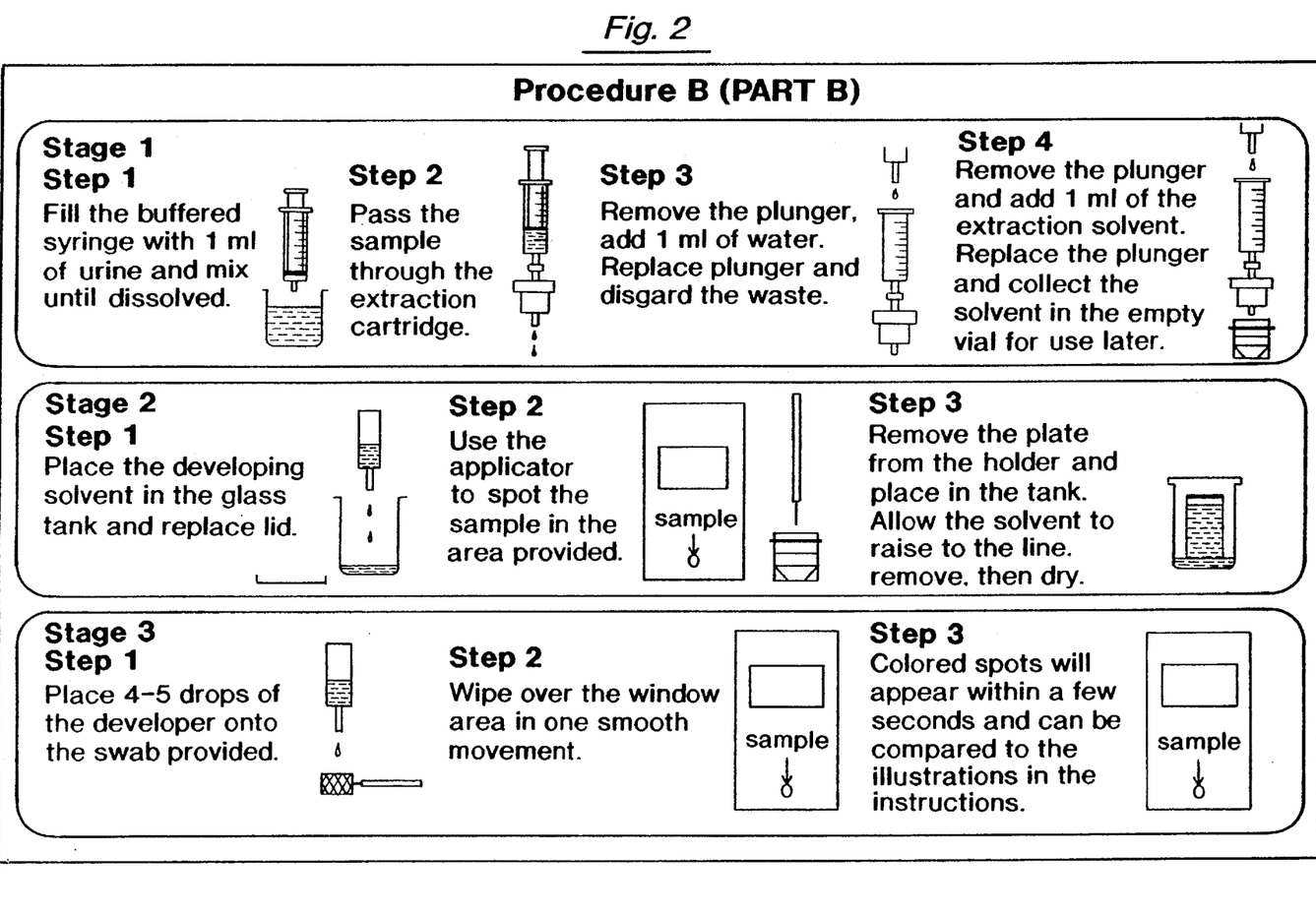
FIG. 2 represents the process steps, apparatus and instructions associated with a "Procedure B" (Part B) of a two part (Parts A and B) procedure described in this patent disclosure.

A Preferred Apparatus For Conducting A Preferred Method Of Detecting o-Hydroxyhippuric Acid In Urine Using the foregoing findings regarding the o-hydroxyhippuric acid/appendicitis relationship, several diagnostic kits for the diagnosis of appendicitis were developed. The most preferred of these diagnostic kits is preferably used in a two part diagnostic test for acute appendicitis. Although use of a two part test kit is preferred, use of the two separate parts which make up the test kit also can be made into two separate and distinct kits which can be employed independently to detect appendicitis. The conjunctive use of the two parts does however, give much more reliable results upon which the diagnostician can make a decision to operate. Again, the function of a diagnostic kit is to provide a convenient method for identifying the chemical substance (o-hydroxyhippuric acid) in the 10 mg/L concentration in order to associate it with appendicitis. Again, this substance, which is frequently referred to as "the marker" for purposes of discussing this apparatus and/or method, is not usually found in urine in concentrations of 10 mg/L or more in blood or urine in healthy patients and its presence in such concentrations indicates inflammation of the appendix. Again, the most preferred embodiment of this particular test can be thought of as a two part test even though the separate parts each have their own separate validity. Part A of the test preferably provides a rapid screening test for the marker (i.e., OHHA) in urine by utilizing a ferric silica reaction to give a color change in the presence of the marker found in the urine of patients with appendicitis. A schematic of the procedure of this test is shown in FIG. 1. Again, this test can be used in its own right to establish the presence (more than a bout 10 mg/L OHHA concentration) or the absence (less than about 10 mg/L OHHA concentration) of appendicitis. Part B, in effect, provides a confirmatory test by using an extraction procedure which is followed by a thin layer chromatographic separation that separates the OHHA. The product of this separation is then visualized with respect to the presence (or absence) of a colored spot. This second procedure (Part B) serves to ensure that a positive test result in the first procedure (Part A) is not due to any contaminating interferences. A schematic of this Part B procedure is shown in FIG. 2.

Chemical Principles Of Procedure

Part A of this preferred test is based on the reaction of the bonded ferric silica matrix which reacts with the marker (σ-hydroxyhippuric acid) in the urine to produce a pink to dark brown or purple color. Part B of this test is preferably split into 3 procedures: (1) solid phase sample extraction to isolate the correct marker as previously described, (2) thin layer chromatography, and (3) development of the marker to provide a visual colored spot which is compared against a control such as a pre-prepared color chart to give positive identification.

Materials To Be Included With The Test Kit

The components of this preferred version of a test kit are intended for use as a unit. However, the elements of Part A and the elements of Part B may themselves comprise separate kits. In any event, the most preferred form of a kit will generally comprise:

| Part A | Color reaction vial |
| --- | --- |
|  | Polyethylene dropper |
|  | Color comparison chart |
| Part B | 3 ml syringe with citrate buffer |
|  | C18 extraction cartridge |
|  | Vial of water wash |
|  | Vial of extraction solvent |
|  | Empty vial for sample collection |
|  | Thin layer plate in holder |
|  | 5 ul spot applicator |
|  | Glass developing tank |
|  | Vial of developer solution |
|  | Control comparison chart |

Specimen Collection For Use In Such Kits

This kit test may be used on any random, freshly voided urine sample. Samples as small as 1 ml can be used. Testing should be done as soon as possible after voiding. It should also be understood that urine preservatives, certain foods and medications may affect test results.

Assay Procedure Part A

1) Add 10 to 15 drops of the urine sample to a 1 ml ferric silica reagent.

2) Recap the vial and preferably invert a few times to assist mixing.

3) The sought after color will develop in a few seconds and will remain stable for several hours. The test result may be read after 20 seconds, preferably in good light and against a white background.

Results Part A

The coloration of the urine to a pink to dark brown or purple color indicates a possible appendicitis. The color can be read directly from a color comparison chart. The color chart most preferably will show a range of positive color reactions together with a negative range. No calculations are required. If Part A is positive, then Part B most preferably carried out to confirm that result. The urine used in Part B is not the same urine used in Part A, but rather is a second part of the urine sample taken from the patient. Part B will also assist in the indication of possible false positive reactions due to other contaminating substances.

Assay Procedure Part B

This test is preferably split into three stages.

Stage 1- Solid phase sample extraction to isolate the marker.

1) Add 1 ml of urine sample to 100 mg of citric acid, then mix gently to dissolve the white crystals.

2) Pass this solution through a previously conditioned C18 extraction tube discarding the output waste urine as it flows through.

3) Pass 1 ml of water through the extraction tube to remove salts and discard the output to waste.

4) Pass 1 ml of methanol through the extraction tube to remove the σ-hydroxyhippuric acid and collect the eluant in a vial and retain for the next stage.

Stage 2- Thin layer chromatography separation.

1) Using a glass TLC tank place 2ml of a solution of 1% acetic acid in methanol in the bottom and place a cap on the top of the jar to reduce evaporation.

2) With the plate placed in a holder (e.g., a cardboard holder), lay the plate/holder on a flat surface. Do not touch the plate at this stage. Using a 5 ul capillary, spot a sample into the center of the hole at the bottom of a card (e.g., a card labelled "Patient Sample") holding the plate. In the case of the requisite concentration of σ-hydroxyhippuric acid, one should see a spot of solvent grow to approximately 1–2 mm.

3) Allow the spot to dry for about one minute (the process may be assisted by gentle blowing). Remove the plate from the cardboard holder and place the plate vertically in a glass jar. Let the solvent in the jar rise up the plate to a line, e.g., to a line 5 mm from the top of the plate. This process will normally take approximately two minutes. Then remove the plate from the jar and allow to dry for one minute and then replace it in the cardboard holder.

Stage 3- Development of the marker to provide a visual colored spot.

4) Using a solution of ferric nitrate in methanol place 4 or 5 drops of the solution onto the absorbent end of a soft swab. Then wipe the wet swab over a window area of the cardboard holder with one smooth movement. One should not press hard on the surface of the plate. Colored spots will appear in the window immediately and the results then can be compared with a control standard.

Results Part B

Results with Part B of this test can be used as a confirmation to Part A. A colored spot in the same vertical position in the plate's developed window as the positive control, indicates a positive result as long as there is no spot that compares to the interference control in the patient's sample (see, generally FIG. 1 and 2).

If a spot is present in the interference control area then it does not necessarily indicate that the test is negative. It does, however, suggest that the patient has been taking some medications that could give false positive indications. The procedure in this situation would be to re-test if possible 12 hours later and continue to re-test until no spot is present in the interference control area. As this particular version of the test is qualitative and only semi-quantitative, the intensity of the colored spot is not relevant. The observation of any clearly defined spot indicates the possibility of appendicitis.

Those skilled in this art will also appreciate that clinical considerations and professional judgment should be applied to the interpretation of the results of these tests. In most instances, clinical diagnosis should not be made on the findings of a single test, but rather should integrate all available clinical and laboratory findings. Nonetheless, the results from these tests do provide very valuable information to aid in the preliminary diagnosis of appendicitis. In screening, negative results from these tests do not totally exclude the possibility of appendicitis since the urinary marker concentration may be too low for detection by this test. Conversely, positive results do not establish a definitive diagnosis without confirmatory evidence of other signs of diagnosis and the assurance of no other influencing factors.

Those skilled in this art will also appreciate that the conditions employed in these various tests will be those appropriate to the particular precipitation agents being used.

It also will be appreciated that o-hydroxyhippuric acid levels in urine samples can be determined by comparing test data to calibration curves created for each individual test using o-hydroxyhippuric acid standard samples. Thus, while the invention has been described by specific examples and preferred embodiments, they are not intended as limitations on the overall inventive concept which is set forth in the following claims.

Thus, having described this invention, what is claimed is:

1. A method for diagnosing appendicitis, said method comprising:

obtaining a urine sample from a human being suspected of having appendicitis; and determining, by a color-producing chemical reaction, that the concentration of o-hydroxyhippuric acid in the urine sample is at least about 10 mg/liter and thereby indicating the probable presence of appendicitis in said human being.

2. A method for diagnosing appendicitis, said method comprising:

obtaining a urine sample from a human being suspected of having appendicitis by virtue of nausea, vomiting or anorexia in association with abdominal pain, which is characteristically present in the periumbilical or right lower quadrant area; and chemically extracting an o-hydroxyhippuric acid component from the urine sample; and determining by a color-producing chemical reaction of the o-hydroxyhippuric acid component that the concentration of o-hydroxyhippuric acid in the urine sample was at least about 10 mg/liter and thereby indicating the probable presence of appendicitis in said human being.

3. A method for diagnosing appendicitis, said method comprising:

obtaining a urine sample from a human being suspected of having appendicitis by virtue of nausea, vomiting or anorexia in association with abdominal pain, which is characteristically present in the periumbilical or right lower quadrant area; and determining by a color producing chemical reaction based upon use of ferric ion that the concentration of o-hydroxyhippuric acid in the urine sample is at least about 10 mg/liter and thereby indicating the probable presence of appendicitis in said human being.

4. A method for diagnosing appendicitis, said method comprising:

obtaining a urine sample from a human being suspected of having appendicitis by virtue of nausea, vomiting or anorexia in association with abdominal pain, which is characteristically present in the periumbilical or right lower quadrant area; and chemically extracting an o-hydroxyhippuric acid component from the urine sample; and determining by a color-producing chemical reaction based upon a reaction of ferric ion and the o-hydroxyhippuric acid component that the concentration of o-hydroxyhippuric acid in the urine sample was at least about 10 mg/liter and thereby indicating the probable presence of appendicitis in said human being.

5. A method for diagnosing appendicitis, said method comprising:

obtaining a urine sample from a human being suspected of having appendicitis by virtue of nausea, vomiting or anorexia in association with abdominal pain, which is characteristically present in the periumbilical or right lower quadrant area; and verifying the presence of o-hydroxyhippuric acid in the urine sample in a concentration of at least 10 mg/liter by reacting the urine with an ion selected from the group consisting of $Fe^{+++}$ or $Cu^{+++}$ capable of entering into a color producing chemical reaction with the o-hydroxyhippuric acid; and comparing the color of a product produced by the reaction of the ion selected from the group consisting of $Fe^{+++}$ or $Cu^{+++}$ and the o-hydroxyhippuric acid with a prepared color comparison chart having a color which correlates with a o-hydroxyhippuric acid concentration of at least 10 mg/liter and thereby indicating the probable presence of appendicitis in said human being.

6. A method for diagnosing appendicitis, said method comprising:

obtaining a urine sample from a human being suspected of having appendicitis by virtue of nausea, vomiting or anorexia in association with abdominal pain, which is characteristically present in the periumbilical or right lower quadrant area;

chemically extracting an o-hydroxyhippuric acid component from the urine sample using a chemical extraction system based upon the use of o-hydroxyhippuric acid—extracting compounds selected from the group consisting of ferric silica, diethylether, butanol, a C18 bonded silica used to place the o-hydroxyhippuric acid component in an aqueous environment or a C18 bond silica used to place the o-hydroxyhippuric acid component in a methanol environment, in order to prepare the o-hydroxyhippuric acid component to undergo a color reaction; and determining that the concentration of o-hydroxyhippuric acid originally in the urine sample was at least 10 mg/liter by subjecting said o-hydroxyhippuric acid component to thin layer chromatography and then noting, with the aid of ultraviolet light having a wave length from about 250 nm to about 360 nm, the presence of a blue fluorescent spot with a retention factor equal to a reference standard based upon known concentrations of o-hydroxyhippuric acid and thereby indicating the probable presence of appendicitis in said human being.

7. A method for diagnosing appendicitis, said method comprising:

obtaining a urine sample from a human being suspected of having appendicitis by virtue of nausea, vomiting or anorexia in association with abdominal pain, which is characteristically present in the periumbilical or right lower quadrant area;

verifying the presence of o-hydroxyhippuric acid in a first portion of the urine sample by reacting the first portion of the urine with an ion of $Fe^{+++}$ bound to a silica gel and which are collectively capable of entering into a color producing chemical reaction with the o-hydroxyhippuric acid;

chemically extracting a o-hydroxyhippuric acid component from the urine sample using extraction chemical systems selected from the group consisting of diethylether, butanol, bonded ferric silica, a C18 bonded silica used to place the o-hydroxyhippuric acid component in an aqueous environment or a C18 bonded silica used to place the o-hydroxyhippuric acid component in a methanol environment; and determining that the concentration of o-hydroxyhippuric acid in the component correlates with a o-hydroxyhippuric acid concentration of 10 mg/L in the urine sample was at least 10 mg/liter by subjecting said component to thin layer chromatography and then subjecting a sample resulting from the thin layer chromatography to a staining procedure, the presence of a blue spot with a predetermined retention factor, and thereby indicating the probable presence of appendicitis in said human being.

8. A method for diagnosing appendicitis, said method comprising:

obtaining a urine sample from a human being suspected of having appendicitis;

performing a first test by reacting a σ-hydroxyhippuric acid component of a first portion of the urine sample with a ferric silica material to produce a color reaction; and performing a second test by: (1) extracting an σ-hydroxyhippuric acid component from a second portion of the urine sample, (2) subjecting the σ-hydroxyhippuric acid component to thin layer chromatography, (3) developing a colored spot on a thin layer chromatography film and (4) comparing the colored spot to a control color chart to determine that the concentration of σ-hydroxyhippuric acid in the urine sample was at least about 10 mg/L and thereby indicating the probable presence of appendicitis in said human being.

9. A kit for determining the presence of σ-hydroxyhippuric acid in human urine in a concentration of at least 10 mg/liter, said kit comprising:

a vial containing a reagent capable of undergoing a color-producing reaction with σ-hydroxyhippuric acid;

means for adding a measured amount of urine to the reagent in order to produce a color reaction; and a color comparison chart having a color which correlates with a σ-hydroxyhippuric acid concentration of at least 10 mg/liter to which the color of a product of the color-producing reaction is compared.

10. A kit for determining the presence of σ-hydroxyhippuric acid in human urine in a concentration of at least 10 mg/L, said kit comprising:

(1) chemical means for extracting σ-hydroxyhippuric acid from a sample of human urine, (2) thin layer chromatography means, (3) a reagent capable of undergoing a color-producing reaction with the σ-hydroxyhippuric acid extracted by the chemical means, and (4) a color comparison chart having a color which correlates with a σ-hydroxyhippuric acid concentration of at least 10 mg/liter to which the color of a product of the color-producing reaction is compared.

11. A kit for determining the presence of σ-hydroxyhippuric acid in human urine in a concentration of at least 10 mg/L, said kit comprising:

a vial containing a chemical capable of undergoing a color-producing reaction with an σ-hydroxyhippuric acid component of the human urine;

a chemical reagent capable of extracting an σ-hydroxyhippuric acid component of the human urine;

thin layer chromatography means for acting upon the σ-hydroxyhippuric acid component;

thin layer chromatography means for developing a colored spot on the thin layer chromatography means; and color chart means for comparing the colored spot to said color chart means to determine that the concentration of σ-hydroxyhippuric acid in the urine is at least about 10 mg/L and thereby indicating the probable presence of appendicitis in said human being.

12. A kit for determining the presence of σ-hydroxyhippuric acid in human urine in a concentration of at least 10 mg/liter, said kit comprising:

a vial containing a ferric silica reagent to which a measured amount of urine is added;

means for adding a measured amount of urine to the ferric silica reagent to produce a color reaction; and a color comparison chart having a color which correlates with a σ-hydroxyhippuric acid concentration of at least 10 mg/liter to which the color of a product of the color reaction is compared.

13. A kit for determining the presence of σ-hydroxyhippuric acid in human urine in a concentration of at least 10 mg/liter, said kit comprising:

a syringe containing a citrate buffer for receiving a measured amount of urine;

an extraction cartridge containing a C18 reagent and having means for receiving a fluid discharge from the syringe;

a vial of water for passing said water through the extraction cartridge containing the C18 reagent after the discharge from the syringe is passed through said extraction cartridge;

a vial of a solvent capable of extracting σ-hydroxyhippuric acid from the C18 contained in the extraction cartridge;

a sample collection vial used to collect a solvent/σ-hydroxyhippuric acid sample from the extraction cartridge;

a tank for holding the solvent/σ-hydroxyhippuric acid sample;

a holder mounted thin layer chromatography plate having a first plate area designated to receive a sample of the solvent/σ-hydroxyhippuric acid sample and a window area to receive a discharge from a swab impregnated with the solvent/σ-hydroxyhippuric acid and dispensing at least a portion of said sample on a window area of said plate;

a swab; and a control standard means having a color which correlates with a σ-hydroxyhippuric acid concentration of at least 10 mg/liter comparing the location and color intensity of spots which appear in a window area of the plate with the control standard means.

14. A kit for determining the presence of σ-hydroxyhippuric acid in human urine in a concentration of at least 10 mg/liter, said kit comprising:

a vial containing a ferric silica reagent to which a first measured amount of urine is added;

means for adding a measured amount of urine to the ferric silica reagent;

a color comparison chart;

a syringe containing a citrate buffer to receive a measured amount of a second measured amount of a urine sample;

an extraction cartridge containing a C18 reagent and having means for receiving a fluid discharge from the syringe;

a vial of water for passing said water through the extraction cartridge containing the C18 reagent after the discharge from the syringe is passed through said extraction cartridge;

a vial of a solvent capable of extracting σ-hydroxyhippuric from the C18 contained in the extraction cartridge;

a sample collection vial used to collect a solvent/σ-hydroxyhippuric acid sample from the extraction cartridge;

a tank for holding the solvent/σ-hydroxyhippuric acid sample;

a holder mounted thin layer chromatography plate having a first plate area designated to receive a sample of the solvent/σ-hydroxyhippuric acid sample and a window area to receive a discharge from a swab impregnated with the solvent/σ-hydroxyhippuric acid and dispensing at least a portion of said sample on a window area of said plate;

a swab; and a control standard means having a color which correlates with a σ-hydroxyhippuric acid concentration of at least 10 mg/liter for comparing positions and color intensities of spots which appear in the window area of the plate with the said control standard means.

15. The kit of claim 14 wherein the vial containing the ferric silica reagent contains approximately 1 ml of ferric silica reagent.

16. The kit of claim 14 wherein the syringe containing the citrate buffer contains approximately 100 mg of citric acid as the citrate buffer and the solvent capable of extracting σ-hydroxyhippuric acid from the C18 is an approximately 1 ml amount of methanol.

17. A method for diagnosing the absence of appendicitis, said method comprising:

obtaining a urine sample from a human being suspected of having appendicitis; and determining, by a color-producing chemical reaction, that the concentration of σ-hydroxyhippuric acid in the urine sample is less than about 10 mg/liter and thereby indicating the probable absence of appendicitis in said human being.

18. A kit for diagnosing the probable absence of appendicitis, said kit comprising: chemical means for reacting σ-hydroxyhippuric acid in human urine to produce a color reaction; means for determining that the concentration of the σ-hydroxyhippuric acid in the human urine is less than about 10 mg/liter; and a color standard means having a color which correlates with a σ-hydroxyhippuric acid concentration of less than about 10 mg/liter to which the color of a product of the color-producing reaction is compared; thereby indicating the probable absence of appendicitis in said human being.

* * * * *